US00PP34878P3

(12) United States Plant Patent
Olesen

(10) Patent No.: US PP34,878 P3
(45) Date of Patent: Jan. 3, 2023

(54) MINIATURE ROSE PLANT NAMED 'POULTY026'

(50) Latin Name: *Rosa hybrida*
Varietal Denomination: Poulty026

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 17/300,620

(22) Filed: Sep. 7, 2021

(65) Prior Publication Data

US 2022/0272884 P1 Aug. 25, 2022

(30) Foreign Application Priority Data

Sep. 21, 2020 (QZ) ..... PBR 2020/2273

(51) Int. Cl.
*A01H 5/02* (2018.01)
*A01H 6/74* (2018.01)

(52) U.S. Cl.
USPC ..... Plt./122
CPC ..... *A01H 6/749* (2018.05)

(58) Field of Classification Search
USPC ..... Plt./122
CPC ..... A01H 6/749; A01H 5/02
See application file for complete search history.

(56) References Cited

PUBLICATIONS

CPVO Register, CPVO Application Consultation (Year: 2022).*

* cited by examiner

*Primary Examiner* — Keith O. Robinson

(57) ABSTRACT

A new garden rose plant of the Miniature class which has abundant, red flowers and attractive foliage. This new and distinct variety has shown to be uniform and stable in the resulting generations from asexual propagation.

2 Drawing Sheets

Botanical designation: *Rosa hybrida.*
Variety denomination: 'Poulty026'.

This application claims priority to Plant Breeder's Rights Application Number 2020/2273, which was filed at the Community Plant Variety Rights Office in the European Union on Sep. 21, 2020, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2013 and the resulting seeds were planted in a controlled environment in Fredensborg, Denmark. The new variety, named 'Poulty026', originated as a single seedling from the stated cross.

The new variety may be distinguished from its male pollen parent and female seed parent primarily by the following characteristics. The male pollen parent plant has a growth height of about 35 cm while the new variety has a growth height of 29 cm. The female seed parent plant has a very dark red flower colour while the new variety has red flowers.

The objective of the hybridization of this rose variety was to create a new and distinct variety with unique qualities, such as:

1. Uniform and abundant red flowers;
2. Vigorous, but very compact growth when propagated on its own roots;
3. Exceptional disease resistance.

This combination of qualities is not present in previously available commercial cultivars of this type, known to the inventor, and distinguish 'Poulty026' from all other varieties of which we are aware.

As part of the rose development program, Mogens N. Olesen germinated the seeds from the aforementioned hybridization during winter of 2013 and conducted evaluations on the resulting seedlings in a controlled environment in Fredensborg, Denmark. 'Poulty026' was selected in the spring of 2014 by the inventor as a single plant from the progeny of the aforementioned hybridization.

Asexual reproduction of 'Poulty026' by rooted cuttings was first done by Mogens N. Olesen in the nursery in Fredensborg, Denmark in July, 2014. This initial and other subsequent asexual propagations conducted in controlled environments have demonstrated that the characteristics of 'Poulty026' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and sterns, of 'Poulty026'.

Specifically illustrated in FIG. 1 of the drawings are open flowers from above and the side, flower petals detached, sepals detached revealing reproductive flower parts and receptacle.

Figure 1:
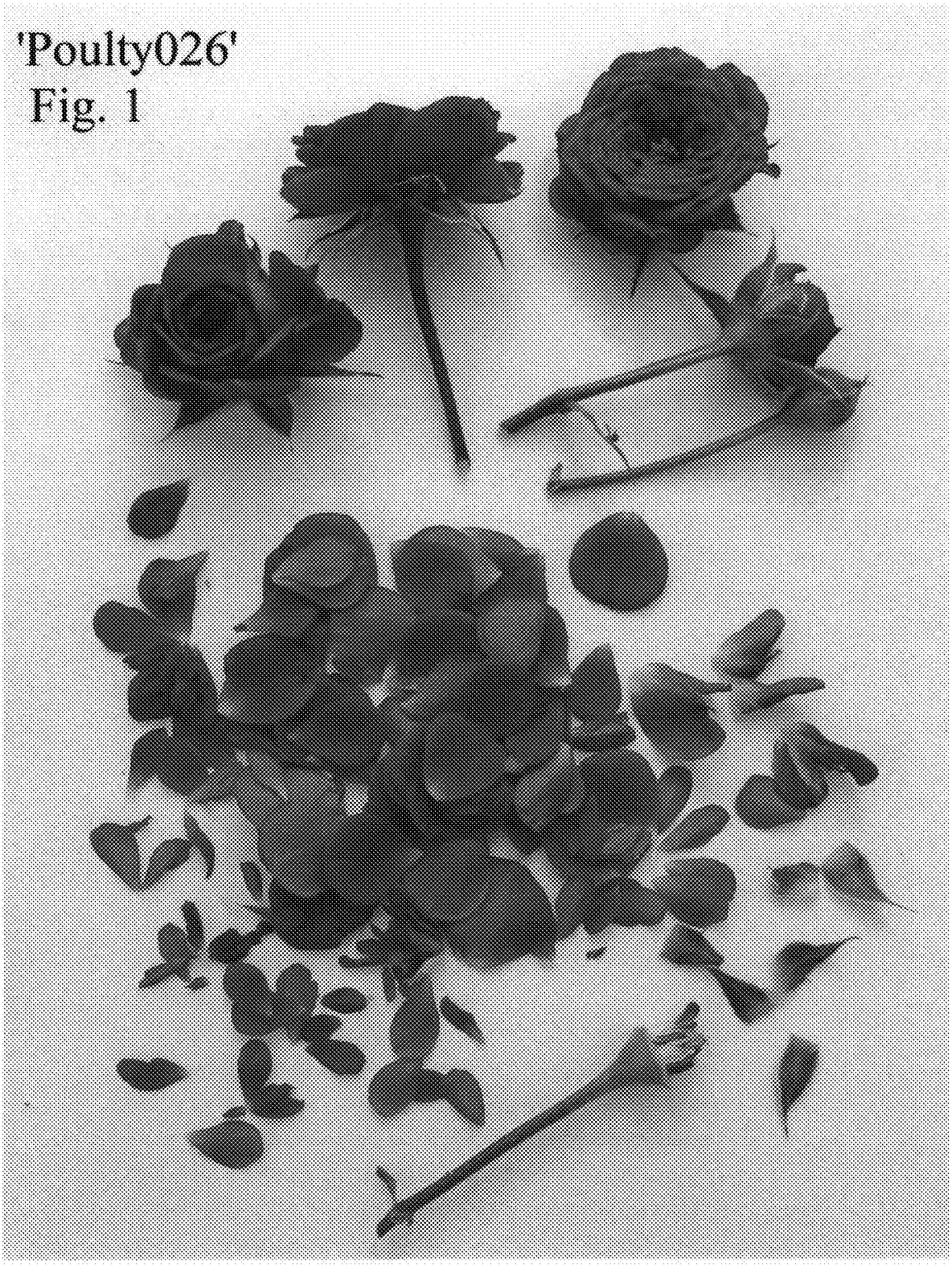
Figure 2:
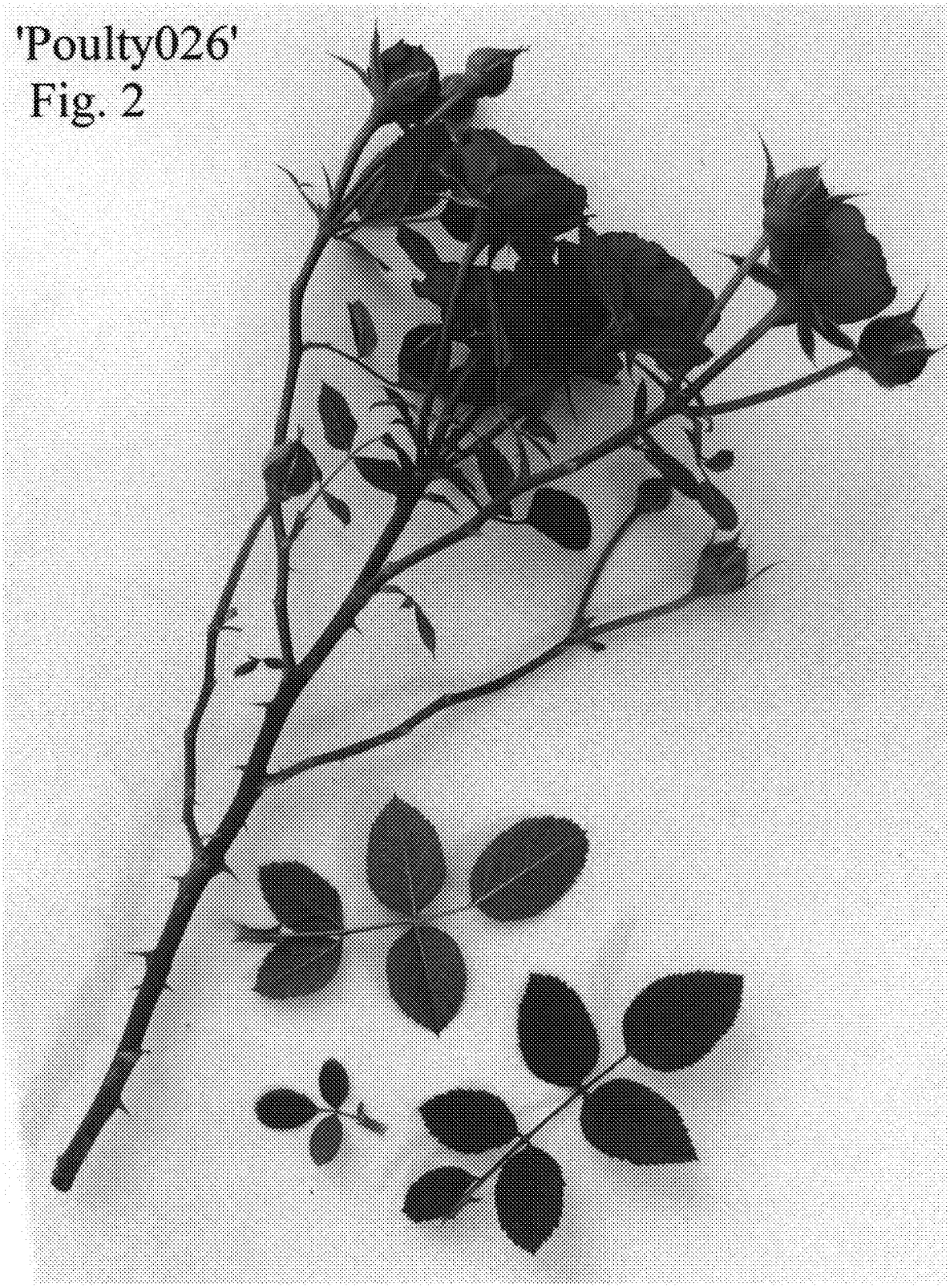

Specifically illustrated in FIG. 2 of the drawings are a flowering branch and mature and juvenile leaves. Plants shown are 4 months in age.

DETAILED DESCRIPTION OF THE VARIETY

The following is a description of 'Poulty026',as observed in its growth in a greenhouse in Odense Denmark. Plants were grown in 24 cm containers under natural light conditions for a period of 6 months.

For a comparison, several physical characteristics of the rose variety 'Poulpar029', U.S. Plant Pat. No. 16,148 are compared to 'Poulty026'. 'Poulpar029'has 30 flower petals, while 'Poulty026' has 185 flower petals. The general tonality of flower colour for 'Poulty026' is Red 46B, while the comparison variety 'Poulpar029' has a tonality of Red 53A. The flower diameter of the applicant variety 'Poulty026' is 47 mm, while the comparison 'Poulpar029' has a flower diameter of 35 mm.

FLOWER AND FLOWER BUD

Blooming habit: Continuous.

Flower bud:

- *Size*.—Upon opening, 20 mm in length from base of receptacle to end of bud. Bud diameter is 14 mm.
- *Bud form*.—Globose.
- *Bud color*.—As sepals divide petals are Red Group 46A.
- *Sepal inner surface*.—Color: Yellow-Green Group 146D. Surface: Lightly pubescent.
- *Sepal outer surface*.—Color: Yellow-Green Group 144A. Texture: Smooth.
- *Sepal shape*.—Apex: Cirrhose. Base: Flat at union with receptacle.
- *Sepal margin*.—Margins have weak foliaceous appendages on three of the five sepals.
- *Sepal size*.—About 23 mm long, 10 mm wide.
- *Receptacle*.—Texture: Smooth. Size: 5 mm in height, 7 mm wide. Color: Yellow-Green Group 144A. Shape: Funnel.
- *Pedicel*.—Surface: Smooth. Length: 30 to 40 mm. Diameter: 2.5 mm on average. Color: Yellow-Green Group 144A. Strength: Strong.
- *Peduncle*.—Length: 1 to 2 cm. Diameter: About 3.5 mm. Color: Yellow-Green Group 144A. Texture: Smooth.

Flower bud development: Flower buds are borne single or clusters of 3 flower buds per stem.

Flower bloom:

- *Fragrance*.—Moderate strength, floral tea rose scent.
- *Duration*.—The blooms have a duration on the plant of approximately 21 days. Petals fall cleanly away from plant after flowers have fully matured.
- *Size*.—Flower diameter is 47 mm when open. Flower depth is 21 mm.
- *Flower shape*.—Rosette, very double flower with many slightly overlapping petals of different sizes.
- *Shape of flower, side view*.—The upper portion is flat. The lower portion is concave.

Petalage: Under normal conditions, flowers have about 185 petals.

General tonality of flower: Open flowers are Red Group 46B.

Petal color:

- *Upon opening, outer petals*.—Upper surface: Red Group 46B. Lower surface: Red Group 53B.
- *Upon opening, inner petals*.—Upper surface: Red Group 46B. Lower surface: Red Group 53B.
- *Basal petal spots, upon opening*.—Upper surface: Yellow Group 4D, about 4 mm in length. Lower surface: Yellow Group 4D.
- *After opening, outer petals*.—Upper surface: Red Group 46B. Lower surface: Red Group 53B.
- *After opening, inner petals*.—Upper surface: Red Group 46B. Lower surface: Red Group 53B.
- *Basal petal spots, after opening*.—Upper surface: Yellow Group 4D. Lower surface: Yellow Group 4D.

Petals:

- *Petal reflex*.—None.
- *Margin*.—Entire and uniform. Moderate undulations.
- *Shape*.—Broad and elliptic. Apex shape: Rounded. Base shape: Acute.
- *Size*.—Varying in length from 7 to 26 mm and in width from 4 to 28 mm.
- *Texture*.—Smooth.
- *Thickness*.—Average.

Petaloids:

- *Size*.—6 mm (l) by 3 mm (w).
- *Quantity*.—About 15.
- *Shape*.—Elliptical with an acute base and acute apex.
- *Color*.—Red Group 46B on the upper surface. Lower surface is Red Group 53B.

Reproductive flower parts:

- *Pollen*.—None observed.
- *Anthers*.—Size: 2 mm in length. Color: Yellow-Green Group 150D. Quantity: About 5.
- *Filaments*.—Color: White Group 155A. Length: 4 mm.
- *Pistils*.—Length: 10 mm. Quantity: 27 on average.
- *Stigmas*.—Color: Greyed-Yellow Group 160B.
- *Styles*.—Color: Green-White Group 157A.
- *Location of stigmas*.—Superior in location relative to the length of the filaments and the height of the anthers.
- *Hips*.—None Observed.

PLANT

Plant growth: Upright and bushy. Plants are 29 cm in height, and 25 cm wide.

Stems:

- *Color of juvenile growth*.—Yellow-Green Group 144B.
- *Color of mature growth*.—Yellow-Green Group 144A.
- *Length*.—Canes are about 14 cm from the base of the plant to the flowering portion.
- *Diameter*.—About 6 mm.
- *Internodes*.—On mature canes about 27 mm between nodes.
- *Surface texture*.—Young wood: Smooth. Older wood: Smooth.

Long prickles:

- *Incidence*.—7 prickles per 10 cm of stem.
- *Size*.—Average length of prickles on mature stems is 8 mm.
- *Shape*.—Upper portion is linear. Lower portion is concave.
- *Color*.—Mature prickles: Greyed-Red Group 179B.

Plant foliage:

- *Compound leaf*.—116 mm (l)×77 (w).
- *Quantity*.—3 or 4 leaves per 10 cm of stern on average.

*Leaf bearing angle to the stem.*—45 degrees.

*Color of juvenile foliage*.—Upper side: Yellow-Green Group 146B & Greyed-Red Group 178B margins. Lower side: Yellow-Green Group 146B with intonations of Greyed-Red Group 178C shaded..

*Color of mature foliage*.—Upper side: Yellow-Green Group 147A. Lower side: Yellow-Green Group 147B.

Plant leaves and leaflets:

*Stipules*.—Size: About 13 mm long, 2 mm wide. Quantity: 2 per compound leaf. Shape: Linear, slightly broad based with outward extending apices. Margins: Finely serrated. Color: Yellow-Green Group 144A.

*Petiole*.—Length: 15 mm. Diameter: 1.5 mm. Upper surface color: Yellow-Green Group 144A. Lower surface color: Yellow-Green Group 144A.

*Rachis*.—Length: About 50 mm. Upper surface color: Greyed-Red Group 178B. Lower surface color: Yellow-Green Group 144A.

*Leaflet*.—Quantity: Normally 5 occasionally 7 leaflets. Margins: Serrated. Size: Terminal leaflets are about 50 mm long, 29 mm wide. Shape: Generally elliptical. Base: Rounded. Apex: Acute or mucronate. Texture: Smooth. Thickness: Average. Arrangement: Odd pinnate. Venation: Reticulate. Glossiness: Not glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulty026', substantially as illustrated and described herein, due to its abundant red flowers, disease resistance, and extended period of bloom.

* * * * *

'Poulty026'

'Poulty026'